(12) United States Patent
Kubek

(10) Patent No.: US 7,229,635 B2
(45) Date of Patent: Jun. 12, 2007

(54) PHARMACOTHERAPEUTIC PROCESS AND COMPOSITION FOR CENTRAL NERVOUS SYSTEM DISORDERS

(75) Inventor: Michael J. Kubek, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 609 days.

(21) Appl. No.: 10/258,222

(22) PCT Filed: Apr. 20, 2001

(86) PCT No.: PCT/US01/12850

§ 371 (c)(1),
(2), (4) Date: Oct. 21, 2002

(87) PCT Pub. No.: WO01/80830

PCT Pub. Date: Nov. 1, 2001

(65) Prior Publication Data

US 2003/0211966 A1    Nov. 13, 2003

Related U.S. Application Data

(60) Provisional application No. 60/198,970, filed on Apr. 21, 2000.

(51) Int. Cl.
*A61F 13/02* (2006.01)
(52) U.S. Cl. ...................................................... 424/434
(58) Field of Classification Search ................ 424/434, 424/489, 501
See application file for complete search history.

(56) References Cited

U.S. PATENT DOCUMENTS

| 3,941,127 A | 3/1976 | Froning |
| 4,849,228 A | 7/1989 | Yamamoto et al. |

(Continued)

FOREIGN PATENT DOCUMENTS

EP       0256726 B       2/1988

(Continued)

OTHER PUBLICATIONS

Born et al., "Sniffing Neuropeptides: A Transnasal Approach to the Human Brain," *Nature Neuroscience*, vol. 5, No. 6, 514-516 (2002).

(Continued)

*Primary Examiner*—Carlos A. Azpuru
(74) *Attorney, Agent, or Firm*—Leydig, Voit & Mayer, Ltd.

(57) ABSTRACT

The present invention is directed to a method of modulating the release of at least one endogenous compound in vivo. The method comprises delivering intranasally at least one micro-construct comprising an agonist and a pharmaceutically acceptable carrier to a locus comprising an agonist receptor and a heterologous receptor that is coupled to at least one common signaling molecule. The micro-construct used in the present inventive method provides sustained release of the agonist provided by erosion of an exterior surface defined by the micro-construct. Once released, the agonist effectively up- or down-regulates at least one signaling molecule common to both the agonist receptor and the heterologous receptor, thereby potentiating or desensitizing the heterologous receptor in order to modulate release of at least one endogenous compound under the control of the heterologous receptor.

24 Claims, 8 Drawing Sheets

U.S. PATENT DOCUMENTS

| | | | |
|---|---|---|---|
| 5,171,812 A | 12/1992 | Domb | |
| 5,360,610 A | 11/1994 | Tice et al. | |
| 5,487,739 A | 1/1996 | Aebischer et al. | |
| 5,652,220 A | 7/1997 | Heya et al. | |
| 5,900,247 A | 5/1999 | Rault et al. | |
| 6,180,603 B1 | 1/2001 | Frey | |
| 6,303,134 B1 * | 10/2001 | Kubek | 424/423 |
| 6,313,093 B1 | 11/2001 | Frey | |
| 6,491,939 B2 * | 12/2002 | Kubek | 424/423 |

FOREIGN PATENT DOCUMENTS

| | | |
|---|---|---|
| EP | 0781550 B | 5/1999 |
| WO | WO 98/08464 A | 3/1998 |

OTHER PUBLICATIONS

Chepurnov et al., "Neuropeptide Thyroliberin—Adaptive Endogenous Anticonvulsant Defense of Brain."

Chepournova et al., "P8/21 Thyrotropin Releasing Hormone (TRH) in Ultra Low Doses Decreases Severity of Seizures in Rats," *Neuropeptides* 26 (Supp. 1):52 (1994) (Abstract).

Domb et al., "Drug Delivery to the Brain Using Polymers," *Critical Reviews In Therapeutic Drug Carrier Systems*, 8(1):1-17 (1991).

Green et al., "$G_i$ Down-regulation as a Mechanism for Heterologous Desensitization in Adipocytes," *The Journal Of Biological Chemistry*, vol. 267, No. 5, pp. 3223-3229 (1992).

Grossman et al., "The Intracerebral Distribution of BCNU Delivered by Surgically Implanted Biodegradable Polymers", *J Neurosurg* 76:640-647 (1992).

Kim et al., "The Long Isoform of Rat Throtropin-releasing Hormone Receptor Down-regulates $G_q$ Proteins," *Journal Biology Chemistry*, vol. 269(31), pp. 19933-19940 (1994).

Kokaia et al., "Seizure suppression in kindling epilepsy by intracerebral implants of GABA—but not by noradrenaline-releasing polymer matrices," *E P Brain Res* 100:385-394 (1994).

Kubek, et al., "Issues Related to Intranasal Delivery of Neuropeptides to Temporal Lobe Targets," Published in: *Proceedings of the 44th Oholo Conference on: The Blood Brain Barrier, Drug Delivery and Brain Pathology*, D. Kobiler, S. Lustig, S. Shapir, Eds., Kluwer Academic/Plenum, New York, 323-350 (2001).

Mason et al., "Thyrotropin-releasing Hormone," *The American College of Neuropsychopharamacology*, http://www.acnp.org/G4/GN401000048/CH048.html, pp. 1-11 (2000).

Milligan, "Agonist regulation of cellular G protein levels and distribution: mechanisms and functional implications," *TIPS*, vol. 14, pp. 413-418, (Nov. 1993).

Mori et al., "Anticonvulsant Effect of DN-1417, a Derivative of Thyrotropin-Releasing Hormone, and Liposome-Entrapped DN-1417, on Amygdaloid-Kindled Rats," *Epilepsia*, 33(6):994-1000 (1992).

Ron et al., "Controlled release of polypeptides form polyanhydrides," *Proc. Nat'l. Acad. Sci. USA*, vol. 90, 4176-4180 (1993).

Saunier et al., "Cyclic AMP Regulation of Gs Protein," *The Journal of Biological Chemistry*, vol. 265, No. 32, 19942-19946 (1990).

Strader et al., "The Family of G-protein-coupled Receptors," *The FASEB Journal*, vol. 9, 745-754 (Jun. 1995).

Tamargo et al., "Interstitial Chemotherapy of the 9L Gliosarcoma: Controlled Release Polymers for Drug Delivery in the Brain," *Cancer Res.* 53:329-33 (1993).

Svoboda et al., "Thyrotropin-Releasing Hormone-Induced Subcellular Redistribution and Down-regulation of $G_{11\alpha}$: Analysis of Agonist Regulation of Coexpressed $G_{11\alpha}$ Species Variants," *Molecular Pharmacology*, 49:646-655 (1996).

* cited by examiner

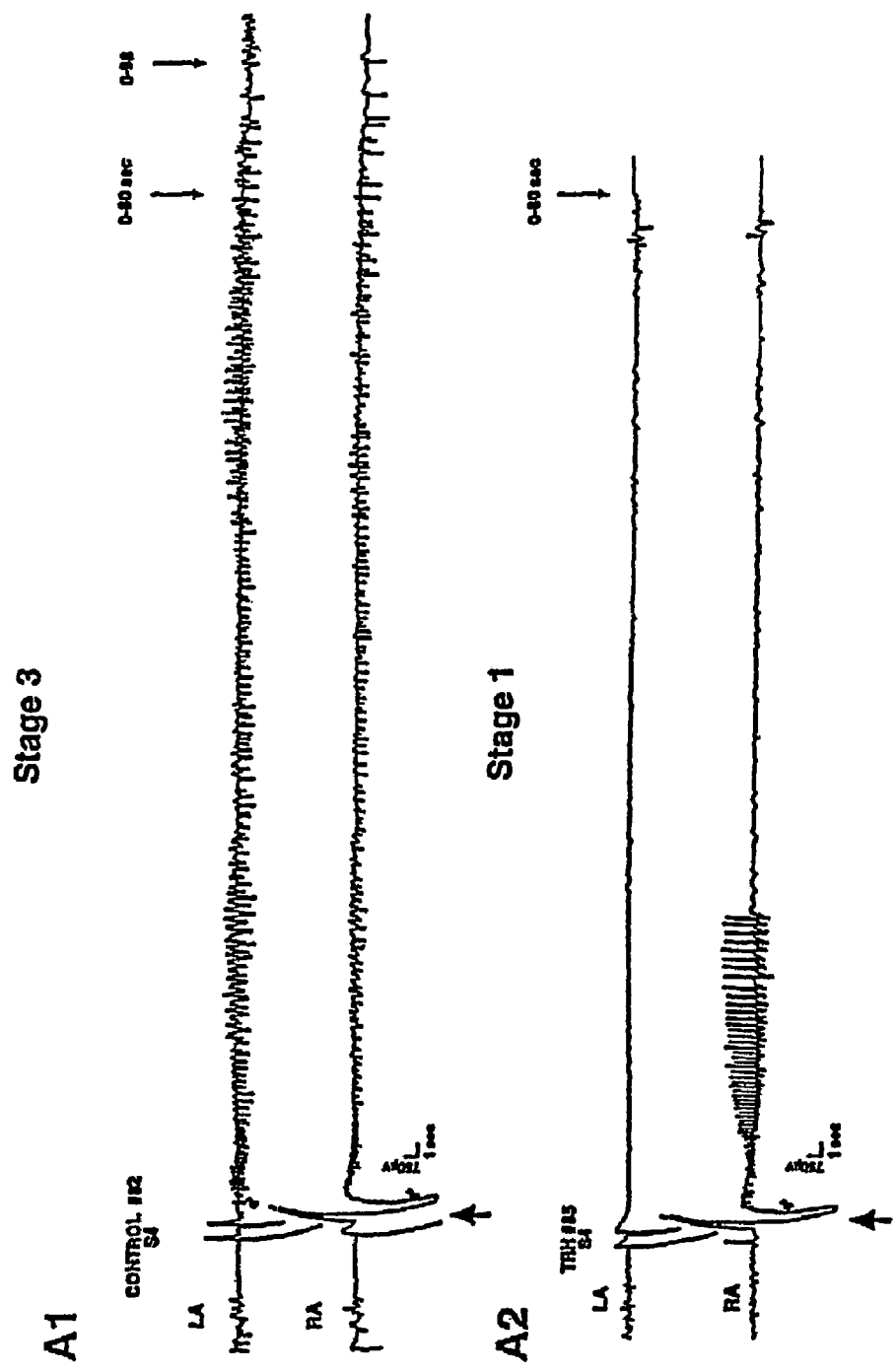

PHARMACOTHERAPEUTIC PROCESS AND COMPOSITION FOR CENTRAL NERVOUS SYSTEM DISORDERS

This application is the U.S. National Phase of International Patent Application PCT/EP01/12850, filed on Apr. 20, 2001, and claiming priority to U.S. provisional patent application No. 60/198,970, filed Apr. 21, 2000, hereby incorporated by reference.

TECHNICAL FIELD

The present invention relates to methods of modulating the release of an endogenous compound. For example, the invention is useful for inhibiting neuropeptide, e.g., glutamate and aspartate, release in, for example, central nervous system (CNS) loci.

BACKGROUND OF THE INVENTION

Therapeutic treatment of various central nervous system disorders has been difficult to achieve because of the failure to provide sustained drug delivery. For example, Thyrotropin-releasing hormone (TRH), an endogenous central nervous system tripeptide, as well as TRH analogs, has been shown to have effective but transient anticonvulsant effects in a variety of animal seizure models. Nevertheless, therapeutic treatment utilizing TRH has been previously unsuccessful in the treatment of epilepsy. In this regard, patients suffering intractable seizures benefited only briefly from repeated TRH and TRH analog treatment.

In particular, oral and injected delivery of TRH and other neural peptides as therapeutic agents have been unsuccessful because of poor penetration of the drug to the desired site. Contributing factors to the limited site-specific bioavailability of therapeutic agents in the central nervous system include rapid peripheral metabolism, poor intestinal absorption, insufficient blood brain barrier penetration, inability to use synthetic precursors, and untoward side effects. As a result, delivering the neural peptide systemically by way of general circulation and/or cerebrospinal fluid would undesirably distribute the neural peptide to nonspecific receptor sites, thereby causing untoward side effects both systemically as well as in the central nervous system.

In U.S. Pat. No. 5,360,610, Tice et at. disclose polymeric microspheres, having diameters ranging from 5 to 45 micrometers, as injectable, drug-delivery systems for delivering bioactive agents to sites within the central nervous system. However, the injectable microspheres described by Tice et al. are ill-suited to provide sustained drug delivery to central nervous system loci because the microspheres tend to disperse in extracellular cerebrospinal fluid (CSF) and are subject to nonspecific uptake and delivery to more distant sites in the brain by CSF through the circumventricular organs, glia and neurons themselves. Larger microspheres are also inadequate because of insufficient rate of release of the bioactive agent from the interior of the microsphere to the site to be treated.

Other prior art approaches for delivering therapeutic agents to central nervous system loci have included osmotic minipumps, attachment to liposomes, and cerebroventricular infusion. These attempts have also been ineffective because osmotic minipumps need replenishment, can become clogged, and are a source of potential cerebral infection. Liposome attachment results in widespread distribution including delivery to nontargeted receptor sites, resulting in untoward side effects. Cerebroventricular infusion results in a short duration of action and widespread distribution to non-targeted receptor sites leading to side effects. Cerebroventricular infusion and osmotic minipumps also require surgery or other invasive procedures in order to deliver compounds to target tissues. The necessity of invasive procedures complicates the generation of a comprehensive therapeutic regimen, including altering the therapeutic agent, increasing or reducing dosage of a therapeutic agent, and the like.

From the foregoing, it will be appreciated that there exists a need in the art for non-invasive, site-specific delivery of a therapeutic agent to central nervous system loci in which sustained release of a therapeutic agent is achieved. It will be appreciated that there also exists a need in the art for non-invasive, site-specific drug delivery in which the release of the drug can be sustained at a relatively constant rate. Accordingly, the present invention provides a non-invasive method for modulating release of an endogenous compound in, for example, central nervous system loci. This and other advantages of the present invention will become apparent from the detailed description provided herein.

BRIEF SUMMARY OF THE INVENTION

The aforesaid problems are solved, in accordance with the present invention, by compositions and non-invasive methods for providing prolonged release of therapeutic agents in situ over time. Under the present invention, micro-constructs are administered intranasally to effectively deliver sustained and controllable release of therapeutic agents, such as neuroactive peptides and/or analogs, in order to treat, for example, neurological disorders. Indeed, the present invention provides a method for modulating release of a predetermined endogenous compound in vivo. The method comprises delivering intranasally at least one micro-construct that includes an agonist and a pharmaceutically acceptable carrier to a locus comprising an agonist receptor and a heterologous receptor, both of which are coupled to at least one common signaling molecule. The micro-construct provides sustained release of the agonist via erosion of an exterior surface defined by the micro-construct. Once released, the agonist effectively up- or down-regulates at least one signaling molecule common to both the agonist receptor and the heterologous receptor to potentiate or desensitize the heterologous receptor, thereby modulating the release of an endogenous compound under the control of the heterologous receptor. Preferably, the pharmaceutically acceptable carrier includes, for example, a polyanhydride, particularly polymerized oleic acid dimers and sebacic acid polymers. For example, a most preferred carrier is an oleic acid dimer identified as poly(FAD-SA).

Advantageously, by providing non-invasive delivery of the sustained release micro-constructs into a locus associated with, for example, a neurological disorder, the present invention eliminates barriers to drug delivery. Also, the micro-constructs of the present invention attenuate the possibility of untoward side effects through intranasal delivery, which confines the long-release micro-constructs to an appropriate locus.

The present invention will be more fully understood upon reading the following detailed description of the preferred embodiments in conjunction with the accompanying drawings.

BRIEF DESCRIPTION OF THE DRAWINGS

FIG. 2A depicts a representative bilateral EEG recording from amygdalae following the fourth in a sequence of kindling stimulation (S4) wherein the upper two tracings represent a control rat identified as number 82, and the lower two tracings represent a TRH-implanted rat identified as number 85.

DETAILED DESCRIPTION OF THE INVENTION

Figure 1:
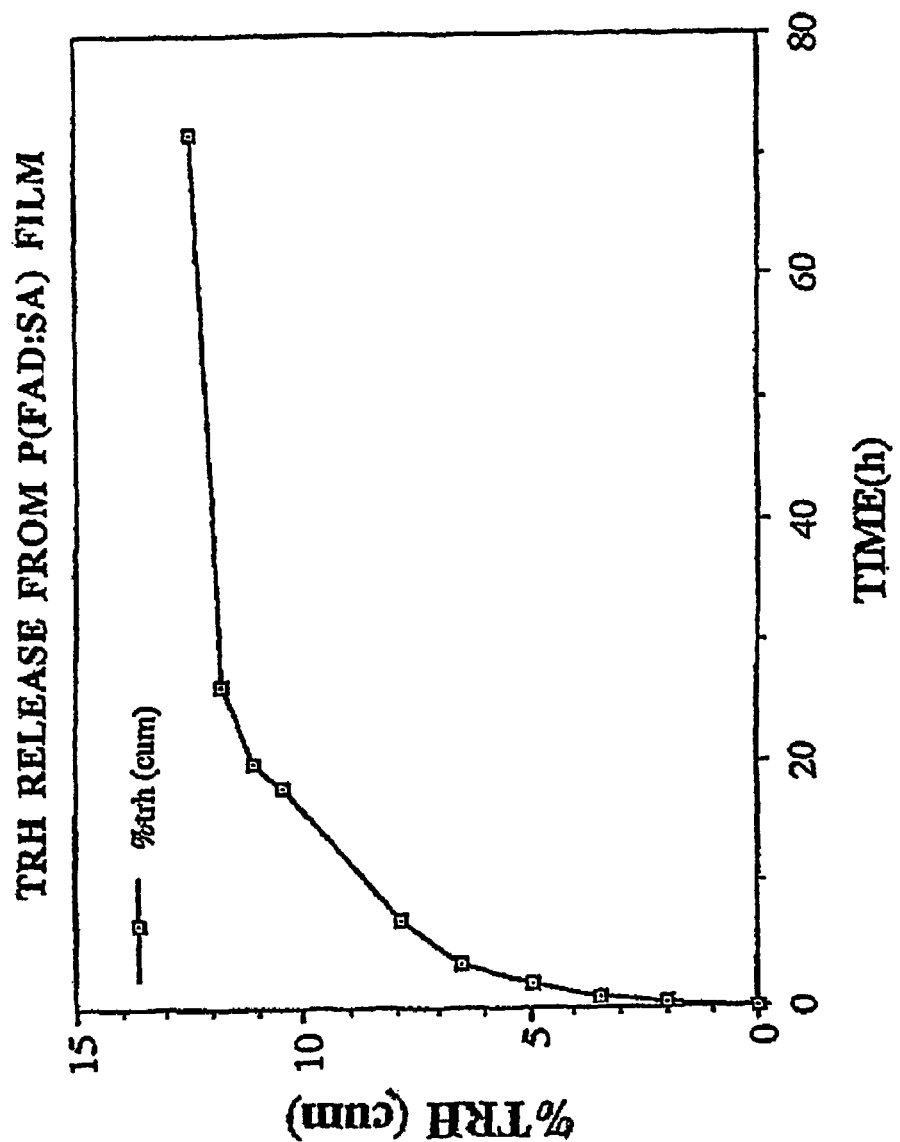
FIG. 1 depicts the rate of TRH release from P(FAD:SA) film.

The present invention is predicated, at least in part, on the surprising and unexpected discovery that intranasal delivery of micro-constructs containing a therapeutic agent is suitable for providing sustained release of the therapeutic agent to neural structures directly or indirectly innervated by the olfactory tract. As such, intranasal delivery of micro-constructs comprising at least one therapeutic agent that modulates signaling in neural loci would be particularly useful in treating a variety of neurological disorders. Therefore, the present invention is directed to a method of modulating the release of at least one endogenous compound in vivo. The method comprises delivering intranasally at least one micro-construct comprising at least one agonist and a pharmaceutically acceptable carrier to a locus comprising an agonist receptor and a heterologous receptor that is coupled to at least one common signaling molecule. The micro-construct provides sustained release of the agonist by erosion of an exterior surface defined by the micro-construct. Once released, the agonist effectively up- or down-regulates at least one signaling molecule common to both the agonist receptor and the heterologous receptor, thereby potentiating or desensitizing the heterologous receptor in order to modulate release of at least one endogenous compound under the control of the heterologous receptor.

The nasal cavity is the first line of defense from airborne pathogens. Yet, the mucosal lining can serve as a locus for drug delivery to the systemic circulation and the brain. Successful systemic peptide delivery has been demonstrated with antidiuretic hormone (vasopressin), calcitonin, and somatostatin (see, for example, Invitti et al., *J. Endocrinol. Invest.* 19:548-555 (1996)). However, successful sustained delivery of neuropeptides directly to specific CNS loci has not been reported.

Solutes entering the nasal cavity typically are destined for three functionally distinct regions: 1) vestibular; 2) respiratory; and 3) olfactory. The olfactory region is the most functionally important site for direct access to the brain and is the major target for intranasal drug delivery to specific sites in the CNS. Three major barriers to neuropeptide bioavailability exist in this region of the nasal cavity. The first barrier consists of tight junctions between the sensory and supporting cells, which prevent blood proteins from crossing the epithelial barrier. Similarly, tight junctions limit the movement of solutes from the apical side of the olfactory epithelium to the submucous space. The second barrier is the viscous mucous layer. The mucous layer contains several proteolytic/hydrolytic enzymes that provide an enzymatic barrier to nasally administered drugs. Peptides are rapidly degraded by specific and nonspecific exo- and endopeptidases in the mucous layer. The third barrier is related to mucous layer clearance. The longer a drug or peptide can remain intact in the mucous layer the greater the probability of being taken up by neural elements of the olfactory epithelium.

Following nasal administration, the pathways of peptide uptake can be classified as (1) olfactory nerve pathway, (2) olfactory epithelial pathway, and (3) systemic pathway. The first two pathways are direct specific and nonspecific CNS routes, respectively, while the third is systemic. Olfactory transduction begins when known or novel volatile odor molecules are inhaled and contact the mucous layer. Odorants bind to odorant binding proteins that deliver the molecules, via cilia, to dendrites of the primary olfactory neuron receptor cells of the olfactory epithelium. Molecules that bind to metabotropic receptors can be internalized at the time of receptor activation, and others can be transported to the cytosol by endocytosis. During intraneuronal transport to the axon terminal, peptides are susceptible to further degradation by cytosolic and lysosomal peptidases. The fate of transported solutes through the olfactory pathway is presently speculative. Primary limbic sites innervated by anterograde olfactory tract fibers include the amygdala, piriform cortex, entorhinal cortex, and adjacent hippocampal formation. Many types of solutes are thought to follow this pathway, such as viruses, dyes, metals and proteins.

For the olfactory epithelial pathway, a solute is thought to enter the olfactory epithelium somewhere other than the receptor neuron. For example, the solute may enter supporting cells or Bowman's gland via pinocytosis or diffusion or, alternatively, it may enter paracellularly through cell junctions into the intercellular fluid. If the solute crosses the basal membrane and enters the lamina propria, it can enter the perineural space around the olfactory nerve where the solute can travel to the much larger volume of the ventricular CSF.

In view of the above, the present invention provides a method for modulating the release of an endogenous compound, wherein the method comprises intranasal delivery of at least one micro-construct comprising at least one agonist and a pharmaceutically acceptable carrier. The micro-constructs of the present inventive method provide sustained release of at least one agonist, such as TRH, by erosion of an exterior surface defined by the micro-construct. The use of micro-constructs that undergo surface erosion has several advantages over agonist-saline formulations, liposome-agonist complexes, or delivery systems relying on bulk erosion such as, for example, systems comprising polylactides (PLA), polyglycolides (PGA), and poly(lactide-co-glycolides) (PLGA). Intranasal delivery of an agonist such as, for example, TRH, in saline, liposome complexes, or micelle-type delivery vehicles provides acute effects, but is quickly inactivated or degraded by enzymes found at several loci of the olfactory pathway, making prolonged or preventative therapy impractical. Delivery systems relying on bulk erosion permit uptake of solutes from the environment, thereby providing inactivating enzymes access to the peptide during the initial burst and the sustained release phases. In light of the many opportunities for degradation of substances delivered intranasally discussed above, bulk erosion results in reduced and inefficient peptide concentrations in vivo. In contrast, surface eroding micro-constructs provide protection against metabolism from cytosolic and extracellular peptidases. The protection provided by surface-eroding micro-constructs can be likened to protection provided by neurosecretory vesicles selectively sythesized by neurons to transport neuropeptides to the axon terminal for storage and subsequent release. In addition to employing surface-eroding microstructures as a means of protecting the agonists from intra-nasal enzymes, the micro-constructs for use in the present inventive method are also preferably non-porous. Non-porous micro-constructs provide an agonist further protection from degrading enzymes. With respect to PLGA, non-porous constructs comprised of PLGA are not sufficiently biodegradable to be suitable for use in the present inventive method. Non-porous PLGA constructs likely build up in a locus upon repeated administration. Therefore, repeated delivery to CNS loci would not be possible with such constructs.

Therefore, a micro-construct providing sustained delivery of at least one agonist via non-bursting surface erosion, wherein the rate of release of the agonist is proportional to the surface area of the delivery system, is the preferred composition for use in the present inventive method. Even more preferred, the micro-construct is non-porous. Desirably, the pharmaceutically acceptable carrier of the micro-construct is a nontoxic polymer that is biodegradable at body temperature. Suitable pharmaceutically acceptable carriers for providing surface-eroding micro-constructs include, for example, polyanhydrides. Desirably, the micro-construct of the present inventive method comprises at least one polymer selected from the group consisting of, but not limited to, polymeric oleic acid dimers, polymeric sebacic acid monomers, and combinations thereof. Ideally, the pharmaceutically acceptable carrier is a co-polymer of fatty acid dimer (FAD) and sebacic acid (SA).

The pharmaceutically acceptable carrier facilitates sustained release and eliminates the possibility of burst release in which there is a large loading dose whereby, for example, 90 percent of the drug is released quickly. In contradistinction, the pharmaceutically acceptable carriers of the present invention are selected to release a relatively constant amount of active therapeutic agent, e.g., agonist, by erosion from the surface over time. More specifically, over a preselected period of time for sustained release, the rate of change of the surface area of micro-constructs such as, for example, microspheres or non-spherical microdisks, can be designed to change relatively slowly, as opposed to the microstructures of the prior art, which will erode through bulk hydrolysis and are therefore subject to a burst release as well as endogenous peptidases. This problem of burst release is compounded when the microstructures increase in size. Whereas in an idealized model, the surface area of a sphere will erode at a rate of $8\pi r$ (dr/dt), where r is the radius and (dr/dt) is the time rate of change of r, the surface area of the micro-constructs of the present invention preferably decrease with erosion at a rate less than $8\pi r$ (dr/dt), preferably at a rate less than about $3.5\pi l$ (dl/dt), where l is a characteristic size of the micro-construct and (dl/dt) is the time rate of change of l. In this regard, the term "characteristic size" refers to a size representative or typical of the micro-construct and, in the case of a microsphere, refers to the diameter of the microsphere, while in the case of a microdisk having thickness much less than radius, refers to the diameter of the microdisk.

In addition, the micro-constructs for use in the present inventive method preferably comprise a substantially uniform density. By "substantially uniform density," it is meant that the micro-construct comprises a solid structure, in contrast to a "capsule" structure wherein, for example, a therapeutic agent is encapsulated within a capsule wall. Use of capsule structures can result in burst release of therapeutic agent or leakage of therapeutic agent through the capsule wall. Contrarily, the micro-constructs for use in the present inventive method provide sustained, controlled release of an agonist. One of ordinary skill in the art will appreciate that the density of a micro-construct as described herein often cannot comprise a completely consistent density throughout the structure, and slight variations may exist throughout the micro-construct. As used herein, "substantially uniform density" is meant to include such variations.

Critically, the micro-constructs form a size and shape that is sufficiently small to allow uptake and trans-neural transport of the micro-construct by olfactory neurons while also providing the necessary surface geometry to provide a relatively constant rate of release of the agonist or therapeutic agent by surface erosion to the desired in situ site. Indeed, the micro-constructs of the present invention include any shape in which erosion of an exterior surface defined by the micro-construct provides sustained release of the agonist. In a preferred embodiment, the micro-constructs are spherical. Alternatively, the micro-constructs can be non-spherical. For example, the micro-constructs can be in the form of microdisks. The most ideal size of the micro-constructs, spherical or non-spherical, will differ depending upon the particular embodiment. However, the size and shape of the micro-construct is such that uptake and transport by olfactory neurons is possible. Therefore, the micro-constructs should range between 5 to 500 nm in diameter. This size range will facilitate uptake and transport in olfactory neurons which range between 200 and 400 nm in size. When non-spherical structures are employed, micro-constructs having diameters significantly larger than the thickness or having a thickness significantly larger than the diameter are most preferred. In addition, the micro-constructs of the present invention can optimize the rate of drug delivery in vivo. Advantageously, the micro-constructs of the present invention, for example, provide sustained release as demonstrated by in vitro tests which show that the sustained release can exceed 70 hours, as seen in FIG. 1. This sustained release is important in view of the mechanism for inhibiting, for example, neurotransmitter release, as described in more detail herein below.

One of ordinary skill in the art will appreciate that the micro-constructs suitable for use in the present inventive method can be produced using methods well known in the art. The concentration of agonist incorporated within the micro-construct will depend upon a variety of factors, including the specific agonist or combination of agonists and the particular pharmaceutically acceptable carrier used. The agonist(s) can comprise from about 1 percent to about 90 percent by weight of the micro-construct. Preferably, the micro-construct comprises from about 1% to about 60% of the agonist(s) in order to optimally control delivery of the agonist through the biodegradable matrix, and more preferably the agonist(s) comprises from about 1% to about 20% of the micro-construct, and still more preferably the agonist(s) comprises from about 1% to about 10% of the micro-construct.

The amount of agonist ultimately delivered to a locus will depend on, for example, the pathology in question, the age and species of the subject, the condition of the disease state, the timing and frequency of administration, as well as the existence, nature, and extent of any adverse side effects that might accompany the administration of the micro-construct and agonist, and the desired physiological effect. Preferably, the concentration of agonist delivered to the locus in vivo is about $10^{-6}$ to about $10^{-12}$ M. The micro-constructs can comprise any agonist to effectively desensitize or potentiate a heterologous receptor and, therefore, have significant utility, for example, in the treatment of many neurodegenerative disorders. For example, micro-constructs comprising TRH or an analog thereof can be used to prophylactically or therapeutically treat neurodegenerative disorders caused by excessive glutamate or aspartate release, such as stroke, epilepsy, ischemia, trauma, sclerosis, Alzheimer's disease and others. As used herein, "prophylactic" treatment refers to the inhibition, in whole or in part, of the onset of a disorder. "Therapeutic" treatment refers to the amelioration, in whole or in part, of a disorder. Delivery of about $10^{-6}$ to about $10^{-12}$ M TRH, for instance, to the brain has been shown to be anticonvulsant in kindling studies (see Example 3 and Chepournova et al., *Neuropeptides* 26:52 (1994)). Also, dosage can vary depending upon the desired psychological effects. For example, lower doses of, for example, TRH and/or TRH analogs can be sufficient to inhibit glutamate release, but in higher doses, the micro-constructs containing TRH and/or TRH analogs can more effectively inhibit both glutamate and aspartate release. Long term intranasal TRH delivery at the concentrations discussed herein through the other defined nasal pathways would not produce CNS and/or endocrine side effects because of three factors: 1) continuous TRH doses are well below those known to induce endocrine effects; 2) significant dilution of the TRH micro-constructs in two large volume compartments (CSF and blood); and 3) continuous metabolism of small quantities of peptide released over time in both compartments. Of course, one of ordinary skill in the art will appreciate that the present inventive method has utility outside the treatment of disease such as, for example, in neurobiological research.

It is to be noted that micro-constructs, such as microdisks or microspheres, are superior to other methods for providing sustained release, such as minipumps. For example, therapeutic agent delivery by micro-constructs is not susceptible to the increased risk of infection found in the use of minipumps. In addition, minipumps are relegated to one site, whereas micro-constructs of the present invention can be advantageously located in several sites. Further, the micro-constructs of the present invention have the advantageous capability of sinusoidal delivery. In this regard, the micro-constructs can be formed with a porous structure, as desired, which can be designed to degrade at differing rates in order to control the release of drug, for example, by selecting differing high and/or low concentration release cycles.

The micro-constructs of the present inventive method are delivered intranasally to modulate the release of a predetermined endogenous compound. Various means of intranasal delivery are well known in the art. The micro-constructs can be delivered, for example, via intranasal insufflators, applicators, sprayers and/or droppers. One of ordinary skill in the art will appreciate that the present invention is not dependent on the particular means of intranasally administering the micro-constructs. However, the micro-constructs are to be delivered in proximity to the olfactory epitheliun region of the nasal cavity in volumes not to exceed 150 µl per nostril to maximize uptake into the olfactory receptor neuron. Any number of micro-constructs can be delivered intranasally to an in vivo locus, so long as a sufficient amount of the agonist is delivered to modulate release of the endogenous compound. In addition, more than one type of micro-construct can be delivered, i.e., micro-constructs comprising different agonists, micro-constructs comprising different carriers, micro-constructs comprising different release rates, etc. Furthermore, the micro-constructs comprising an agonist and a pharmaceutically acceptable carrier can be co-administered with other agents appropriate for nasal delivery. Preferably, the micro-construct is co-administered with a natural odorant to enhance uptake and release at neuronal target sites.

The micro-constructs also can be co-administered with at least one neuronal transport enhancer that facilitates transport of the micro-constructs along microtubules. Intraneural transport mechanisms have been defined in a wide range of nerves (Ochs and Brimijoin, *Peripheral Neuropathy*, Axonal Transport, In Dyck et al. (Eds.), Saunders, Philadelphia, 331-360 (1993)). The neuronal organelle most likely responsible for axonal transport is the microtubule. In anterograde transport, materials are attached to transport enhancers, such as kinesins, and moved along microtubules. Transport enhancers associated with the kinesin family of peptides include, but are not limited to, Nkin, Unc104/KIF, and Fla/KinII. For retrograde transport of the micro-construct, dyneins, i.e., MAP-1C, can be employed. Thus, co-administration of intraneuronal transport enhancers, e.g., factors that aid in movement along microtubules, aid in the delivery of the agonist to target areas. The transport enhancer can be present in the formulation comprising the micro-construct such that the transport enhancer is co-delivered intranasally. Alternatively, the transport enhancer can be incorporated into the micro-construct, along with the agonist, such that the transport enhancer is made available to microtubules by erosion of the surface of the micro-construct.

In some embodiments of the present inventive method, TRH-containing micro-constructs comprised of a co-polymer of fatty acid dimers and sebacic acid (TRH-P (FAD:SA)) are employed. TRH-P (FAD:SA) micro-constructs, indeed all surface-eroding micro-constructs, provides several advantages over the delivery systems involving bulk erosion. For example, the surface eroding characteristics of the TRH-P(FAD:SA) micro-constructs protects the peptide from proteolytic enzyme penetration in the mucous membrane layer. Therefore, the need for proteolytic enzyme inhibitors is eliminated. The administration of proteolytic enzyme inhibitors, as required by some bulk-eroding delivery devices, could upset the delicate balance (dynamic equilibrium) among naturally occurring proteinases, endopeptidases, and proteinase inhibitors needed by the nasal epithelium for protection against xenobiotics. In addition, P(FAD:SA) is a fatty acid dimer that enhances absorption of the micro-construct in the olfactory mucociliary substrate, thereby increasing the probability of olfactory neuron uptake and transport by either active or passive mechanisms. Several classes of compounds including fatty acid salts such as, for example, sodium caprylate, have been developed as absorption (permeation) enhancers and are known in the art (Agarwal et al. *Indian J. Exp. Biol.* 37:

6-16(1999)). Furthermore, P(FAD:SA) micro-constructs will not penetrate or disrupt tight junctions between sensory and supporting cells. Thus, the cellular integrity of the epithelial lining in this region remains intact and functional. Collectively, the properties of the surface-eroding TRH-P (FAD:SA) micro-construct formulation enhances bioavailability to the receptor neuron for uptake and transport specifically through the olfactory pathway.

One of ordinary skill in the art will appreciate that the present invention is not limited by the specific locus selected for agonist delivery. For example, TRH can have efficacy in any part of the central nervous system but is more applicably efficacious in regions where the density of TRH receptors (the "agonist receptor") is high, particularly, in the amygdala, the hippocampus and other limbic system structures and neocortex. The micro-constructs of the present inventive method are delivered to a locus comprising an agonist receptor and a heterologous receptor. The agonist receptor and heterologous receptor are coupled to at least one common signaling molecule. As such, the agonist receptor and heterologous receptor are present in or on the same cell. Preferably, the heterologous receptor and agonist receptor are G-protein linked. However, the present inventive method can work through other signaling molecules and pathways. For example, the agonist may modulate the heterologous receptor through a non-receptor signaling cascade that leads to potentiation or desensitization of the heterologous receptor. Release of the endogenous compound to be modulated is under the control of the heterologous receptor.

Referring now to the mechanism of action, the present invention has particular utility in providing an agonist that can modulate release of endogenous compounds, such as neurotransmitters, neuropeptides or hormones, by way of a novel mechanism of potentiating or desensitizing a heterologous receptor by downregulating signal transduction pathways, e.g., signaling pathways involving G-proteins, common to both the agonist, or homologous, receptor and the heterologous receptor that is selected for potentiation or desensitization. As used herein, "agonist receptor" refers to a receptor, located intracellularly or on the cell surface, that recognizes and/or binds the agonist. Also, "heterologous receptor" refers to a receptor, located intracellularly or on the cell surface, that does not necessarily bind the agonist, but, instead, controls the release of an endogenous compound. A number of conditions are important in the present mechanism for achieving prolonged heterologous receptor desensitization or potentiation. For example, the agonist receptor and the heterologous receptor preferably are highly expressed in the same cell. In addition, the agonist and heterologous receptors utilize at least one common signaling molecule, e.g., the same G-protein signaling system, such as $G_i$ or $G_q$. When heterologous receptor desensitization is desired, the agonist receptor must be downregulated, that is, effectively reduced, by its transmitter/modulator and agonists. Also, the downregulation of the agonist receptor must be associated with downregulation of, for example, the G-protein shared by the heterologous receptor. Critically, sustained homologous (agonist) receptor exposure with the agonist is required for prolonged desensitization to occur. One of ordinary skill in the art will appreciate that potentiation of a heterologous receptor is also dependent on the conditions set forth above. Therefore, the present inventive method can be used to effectively desensitize a heterologous receptor, thereby inhibiting the release of an endogenous compound linked to that receptor or modulating its receptor-mediated effects. On the other hand, the present inventive method is used to potentiate a heterologous receptor, thereby increasing the release of an endogenous compound under the control of the heterologous receptor.

Using the guidelines described above, the ordinarily skilled artisan can select the appropriate agonist receptor for modulating a particular heterologous receptor(s). The receptor-mediated signalling cascade has been ellucidated for several families of G-protein coupled receptors (see for example, Watson & Arkinstall, The G-protein linked receptor facts book, Academic Press, 1994). A given agonist receptor and an appropriate G-protein sharing heterologous receptor(s) to be modulated is identified to be co-localized to the same cell. Sustained delivery of agonist to its homologous receptor affects both homologous and heterologous receptor signalling events.

As an example, the following discussion refers to modulation of the release of an endogenous compound in the form of inhibition of glutamate release, but it will be appreciated that this discussion is merely exemplary and is not limiting to the present invention. It will be appreciated that the mechanism of the present invention will also function to modulate second messenger systems, including increasing release of a predetermined endogenous compound by upregulating components of a signal transduction pathway, e.g., G-proteins, common to the agonist receptor and heterologous receptor, thereby potentiating the heterologous receptor.

By way of background, metabotropic glutamate receptors (mGluRs) make up a small portion of the much larger superfamily of G-protein linked receptors consisting of seven transmembrane spanning regions coupled to second messenger systems, such as adenylyl cyclase/cAMP, phospholipase-C (PLC)/DAG, and IP3, by a class of GTPases termed G-proteins. It is now recognized that a large proportion of the neurotransmitters (histamine, epinephrine, glutamate, GABA, acetylcholine, dopamine, serotonin, norepinephrine, etc.), neuropeptides (TRH, somatostatin, neuropeptide-Y (NPY), tachykinins, opiods, cholecystokinin (CCK), neurotensin (NT), etc.), and hormones (glucagon, melatonin, ACTH, etc.), act through G-protein linked receptors. Presently, eight different mGluR subtypes ($mGluR_{1-8}$) have been cloned and subsequently expressed in various cell lines. The mGluRs have been classified into three groups (Groups I-III) based on amino acid sequence similarity, agonist/antagonist pharmacology and signal transduction pathways to which they couple. The mGluRs are believed to modulate glutamate synaptic transmission via both presynaptic and postsynaptic mechanisms. It is known that activation of Group I receptors (and ionitropic receptors (iGluRs)) induces seizures and appears to contribute to excitotoxicity and cell death. In contrast, activation of Group II/III mGluRs reduces glutamate release and produces neuro-protective effects.

It is clear that several ligand-initiated events are affected by both endogenous transmitter and agonist/antagonist receptor interactions. Recent data have shown that G-proteins are critical in signal transduction pathways involving glutamate release and, when downregulated, can affect activity of both the agonist-specific and a heterologous (non-agonist-specific) receptor that utilizes the same G-protein signaling cascade. It should be noted that, of all the glutamate receptors, only mGluRs utilize G-protein coupling. Moreover, of the three mGluR subgroups, only Group I mGluRs use $G\alpha_{q/11}$ for signal transduction. $G\alpha_{q/11}$ refers to the α subunits of the $G_q$-like G-proteins, $G_{q/11}$, that have been observed to play a key role in the regulation of intracellular $Ca^{++}$ levels and in the generation of second messenger systems. Importantly, it is well recognized that $G\alpha_{q/11}$ G-proteins couple the TRI receptor (TRHR) to PLC for cell signaling. The TRHR is known to be significantly downregulated by sustained exposure to ligand. TRHR's are also known to be downregulated following seizures in neurons that co-localize glutamate and TRH, as well as their receptors.

Agonist receptor downregulation is essential for G-protein downregulation. In this regard, it has been previously demonstrated that sustained exposure (16 hr.) of TRH to cloned TRHRs results in substantial subcellular redistribution and marked dose-dependent downregulation of $G\alpha_{q/11}$ G-proteins without affecting cellular levels of the other Group I subunits. Group I mGluRs are the only glutamate receptors that require the $G\alpha_{q/11}$ subunit to affect presynaptic glutamate release and postsynaptic ion channel effects, and sustained TRH exposure to its receptor results in relocation and substantial (20-70%) reduction of $G\alpha_{q/11}$ G-proteins. Therefore, the prolonged exposure of the TRHR (against receptor) to ligand (agonist), such as that released from TRH-polyanhydride micro-constructs of the present inventive method, uncouples $G\alpha_{q/11}$ from the Group I mGluR (heterologous receptor) in cells that express both the TRHR and Group I mGluRs. Uncoupling of $G\alpha_{q/11}$ from the mGluR results in prolonged Group I desensitization to pre- and postsynaptic glutamate stimulatory effects and potentiation of Group II/III inhibitory effects. As such, glutamate release is inhibited.

This mechanism can account, in large part, for TRH effects observed on inhibition of glutamate release and suppression of neuronal $Ca^{++}$ uptake. This novel mechanism of prolonged desensitization of Group I mGluRs by sustained TRH release in situ could account for the enhanced and prolonged duration of antiepileptogenic and anticonvulsant effects of TRH in the kindling model of temporal lobe epilepsy. This effect would not be limited to seizures and its related cell damage, but could include modulation of other proposed excitotoxic effects of excessive glutamate release including, for instance, neurodegeneration associated with neurotrauma, stroke, ischemia and Alzheimer's dementia. Thus, it is clear that heterologous desensitization by TRH could modulate other G-protein receptors that utilize $G\alpha_{q/11}$ coupled signaling cascades.

Therefore, in a preferred embodiment, the modulated endogenous compound is glutamate, the agonist is TRH, and the heterologous receptor comprises a glutamate receptor. However, in view of the above, one of ordinary skill will appreciate the potential of the present inventive method to modulate the release of numerous endogenous compounds including, but not limited to, glutamate. For instance, the modulated endogenous compound can be selected from a neurotransmitter, a neuropeptide, or a hormone. Suitable neurotransmitters include, for example, histamine, GABA, acetylcholine, serotonin, norepinephrine, epinephrine, glutamate, and dopamine. Neuropeptides include, for instance, TRH, somatostatin, NPY, CCK, tachykinins, opioids and NT. Hormones to be modulated by the present inventive method include, but are not limited to, glucagon, ACTH and melatonin. Of course, the release of other endogenous compounds can be modulated by the present inventive method, so long as release of the endogenous compound is under the control of a heterologous receptor.

In order to promote a further understanding and appreciation of the present invention and its attendant advantages, the following specific examples are provided.

EXAMPLES

The following examples further illustrate the present invention but, of course, should not be construed as in any way limiting its scope.

Example 1

This example illustrates a preferred method of preparing micro-constructs comprising an agonist and a pharmaceutically acceptable carrier for use in the present inventive method.

TRH micro-constructs were produced from an anhydride copolymer of fatty acid dimer (FAD) and sebacic acid (SA) in a 50:50 ratio according to known methods. Briefly, Poly(FAD:SA) (500 mg, MW 8,600) was melted (60-65° C.) and synthetic TRH (20 mg, Bachem, Calif., MW 362) was added to the copolymer to yield a 4% concentration by weight. The melted polymer mixture was cast between two glass plates and allowed to cool to room temperature resulting in a uniform film approximately 0.2 mm thick. An estimation of TRH release characteristics was determined in vitro by placing a 10% TRH carrier film in 0.1 M phosphate buffer, pH 7.4, at 37° C. Aliquots were taken periodically to determine the peptide concentration in the buffer using a known method. TRH release from the Poly(FAD:SA) co-polymer was first order for the first 19-20 hours with no initial TRH burst. A constant 12% rate of TRH release was obtained thereafter up to 70 hours, the last sampled time point (FIG. 1). Having determined its release characteristics, the films were packaged in sealed foil envelopes for storage. Immediately before administration, disk-shaped micro-constructs (0.4 mm dia.×0.2 mm thick) were punched from films using a specially constructed 22 gauge cannula containing a delivery stylet.

Example 2

The following example demonstrates the ability of an agonist, TRH, to inhibit [$K^+$] stimulated glutamate release from hippocampal slices in vitro.

Figure 6:
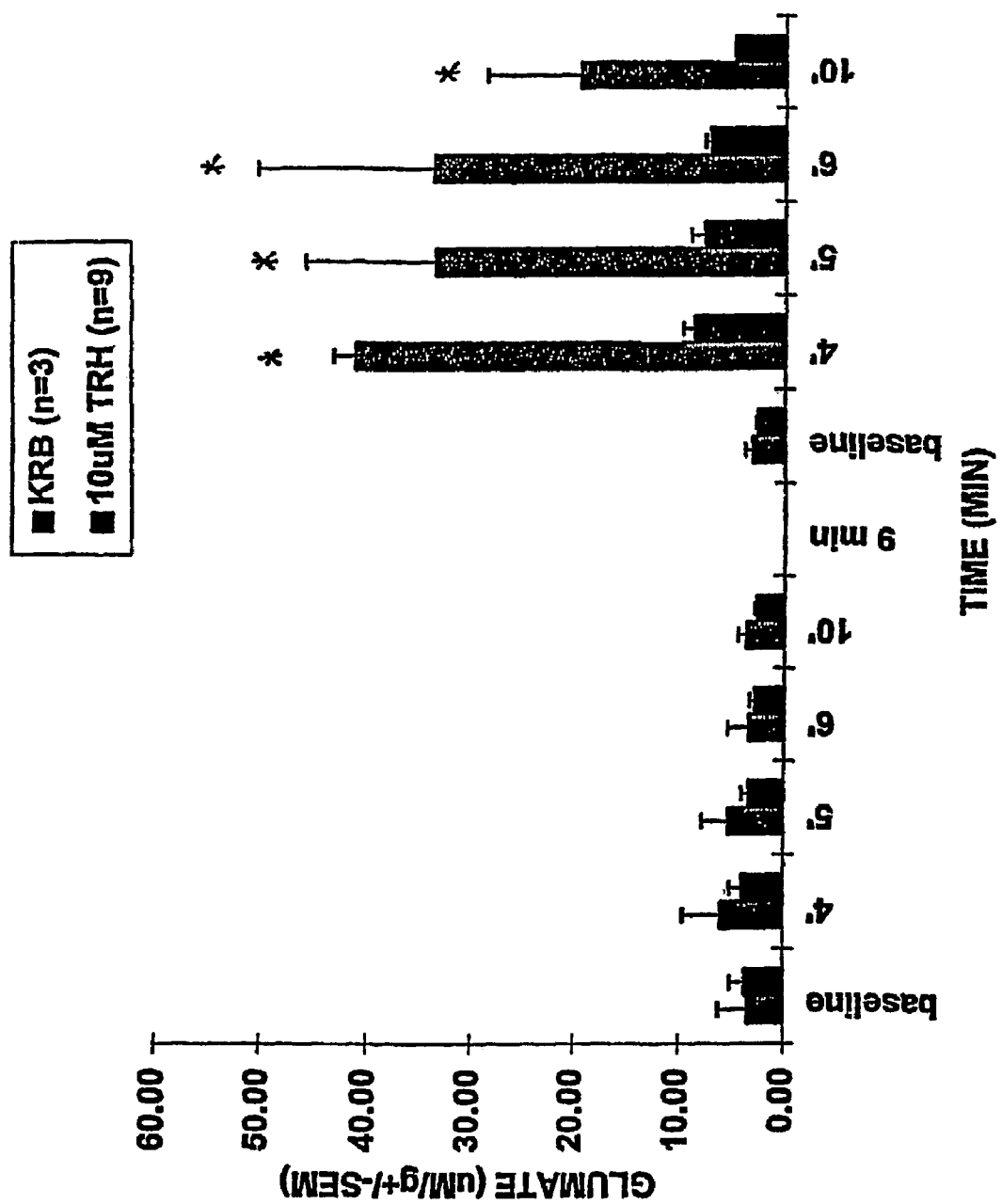
FIG. 6 is a graph illustrating prolonged inhibitory effect of TRH on potassium stimulated glutamate release.

Enhanced excitatory amino acid release is suspected in pathways associated with seizures and excitotoxicity. In this regard, superfused hippocampal slices were used to investigate whether TRH could inhibit glutamate release in vitro. Rat hippocampi were removed and sliced transversely (500/μm) under low magnification. Slices were weighed, washed in cold saline, transferred to individual tissue chambers floated in a 37°/C. water bath, and were equilibrated in oxygenated (95% $O_2$/5% $CO_2$) Kreb's buffer (KRB) at 37° C. for 120 min. (0.5 ml/min). Slice chambers were then superfused 10 min. with KRB (control), or KRB containing 10 μM, 1 μM, or 0.1 μM TRH, respectively, prior to 5 min. stimulation with modified KRB (50 mM [$K^+$]±TRH). Fractions (1 min.) were collected during the 5 min. stimulation and for an additional 10 min. (0.5 ml/min.) thereafter, and analyzed for glutamate by HPLC. Data were expressed as μMg/fraction±S.E.M. All three TRH doses significantly ($p<0.001$), but not dose-dependently, inhibited peak 50 mM [$K^+$]-stimulated glutamate release (48.05±8.59 vs 2.35±0.50, 1.54±0.33, 1.38±0.28, respectively) and glutamate remained below control ($p<0.05$) at 10 min. post stimulation (4.37±1.29 vs 1.35±0.48, 1.11±0.26, 1.54±0.43, respectively). As seen in FIG. 6, perfusion (5 min.) with KRB+10 μM TRH significantly ($p<0.05$) blocked glutamate release by 50 mM [$K^+$] stimulation given 15 min. later.

These results are the first to show a potent and prolonged inhibitory effect of TRH on glutamate release in vitro. It is suggested that endogenous TRH is anticonvulsant/neuroprotective and, in part, functions to modulate glutamate release in certain neurological disorders such as epilepsy.

Example 3

The present example illustrates the ability of micro-constructs comprising an agonist to modulate expression of an endogenous compound in vivo. In particular, this example demonstrates the ability of micro-constructs comprising TRH, when implanted into central nervous system loci, to control the rate of seizure spread in vivo.

Details of our kindling paradigm have been established previously. Briefly, male Sprague-Dawley rats (300-325 g) (Harlan Industries, Indianapolis) were housed in plastic cages. All animal care and handling was conducted in compliance with the Animal Welfare Act and adhered to principles set forth in the *Guide for the Care and Use of Laboratory Animals*, National Institutes of Health publication 86-23, 1985 edition. Animals were anesthetized with pentobarbital sodium and ketamine (40 mg/Kg, i.p.) at the time of surgery. A cannula for delivering microdisks was inserted into the right basolateral amygdalal at coordinates 2.8 mm posterior and 5.0 mm bilateral to the bregma, and 8.5 mm below the surface of the skull. A disk-shaped micro-construct (microdisk) containing 90 μg Poly(FAD:SA), 4% TRH (3.6 μg) was inserted into the right basolateral amygdala through the cannula using a stylet. A second group of rats was implanted with a microdisk (2×3.6 μg). A third group of control rats was implanted with a microdisk of 90 μg Poly(FAD:SA) without TRH. After resting 10 min., the cannula was removed. Bipolar electrodes where then implanted bilaterally into the amygdalae. The stereotaxic coordinates were 7.9 mm ventral to the surface of skull. A reference electrode was inserted in the skull overlying the anterior cortex as previously described. Immediately following and three days after surgery, all animals received 50 mg nafcillin (i.m.) to eliminate possible infection. Animals were observed for overt behavioral changes immediately after surgical recovery and throughout the study.

Five days after surgery, the afterdischarge (AD) threshold was determined, and a kindling stimulus of 200 μA was delivered once daily as previously described. The duration of evoked AD and severity of behavioral seizures were recorded following each stimulation session. Behavioral seizures were scored according to a known method, namely: Stage 1, motor arrest, facial automatism, chewing; Stage 2, chewing, and head nodding; Stage 3, forelimb clonus; Stage 4, rearing and forelimb clonus; Stage 5, rearing with forelimb clonus and failing. Animals having three consecutive Stage 5 seizures where considered fully kindled. After reaching fully kindled status, the animals were maintained in their home cages for an additional 30-40 days until a final stimulus was given to determine if the animals remained kindled. During this period, any animals that lost head caps were removed from the study.

Repeated measures analysis of variance (ANOVA) following the general linear models procedure was used in statistical analysis of the AD and clonus duration data. Statistical comparisons of the kindling stages data and afterdischarge threshold (ADT) data were made using the Kruskal-Wallis ANOVA by ranks. One-tailed Student's t-tests were used for mean comparisons of kindling permanence at the termination of the study. Data are expressed as MEAN±S.E.M. with (n) the number contributing to the mean. In all cases differences were considered significant at $p<0.02$.

It was determined whether the control polyanhydride microdisks or the TRH microdisks had an effect on the afterdischarge threshold (ADT). All threshold currents were in the range required for kindling to occur (40-100 μA). No statistical differences in stimulating currents were observed among or between right (microdisk) and left (no microdisk) ADT's.

Animals implanted with one or two TRH microdisks required significantly more stimulations (2-fold) to reach each of the five behavioral kindling stages and twice the number of stimulations (8.63±0.924 vs. 16.67±1.369; $P<0.02$) to become fully kindled. This outcome resulted from only one implantation in the seizure focus (stimulated amygdala) and covered a period between 20 to 30 days post implantation. Since no statistically significant difference was observed between implanting one and two microdisks with TRH, only results of a single microdisk implant are presented.

Representative bilateral EEG recordings from the amygdalae after the fourth (S4) and seventh (S7) kindling stimulations are shown in FIGS. 2A & B, respectively. Following S4, prolonged (>90 sec.) bilateral AD's were recorded in the control animal (A1), whereas, in the TRH-microdisk subject, (A2) the AD duration in the stimulated amygdala was noticeably shorter while no AD was recorded in the contralateral amygdala. Behaviorally, S4 resulted in a Stage 3 response in the control rat, whereas, it produced only a Stage 1 response in the TRH-microdisk animal. An S7 control animal (B1) experienced bilateral AD's greater than 130 sec., whereas in the TRH-implanted subject (B2), the AD duration in the stimulated amygdala was strikingly shorter. Moreover, no AD's were recorded in the contralateral amygdala. Behaviorally, S7 resulted in a Stage 5 generalized seizure in the control animal. This is in marked contrast to only a Stage 2 response in the TRH-microdisk subject (B1 vs B2).

Figure 2B:
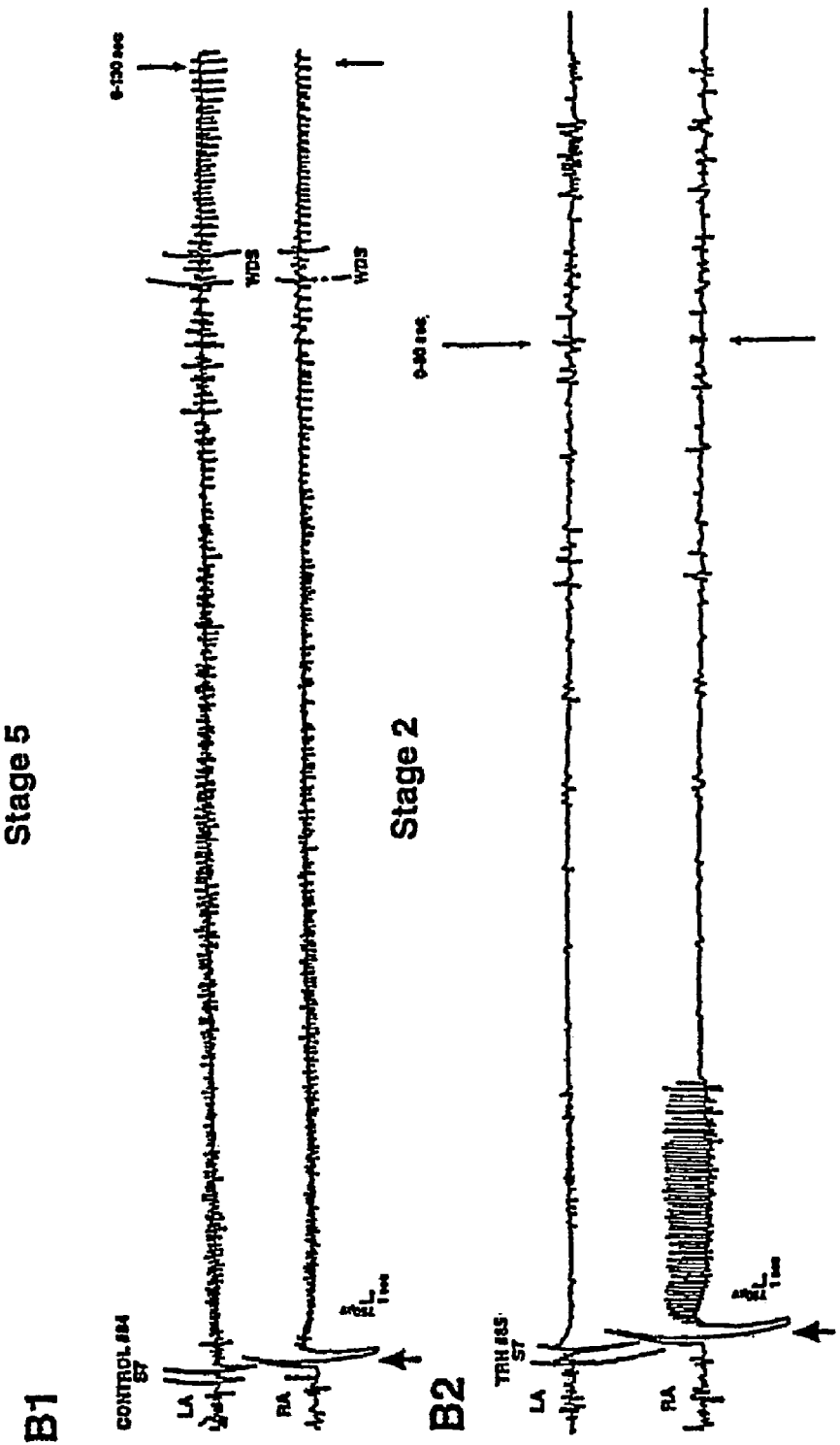
FIG. 2B depicts a representative bilateral EEG recording from the amygdalae after a seventh kindling stimulation, identified as S7, wherein the upper two tracings represent a control rat identified as number 84, and the lower two tracings represent a TRH-implanted rat identified as number 85.
Figure 3A:
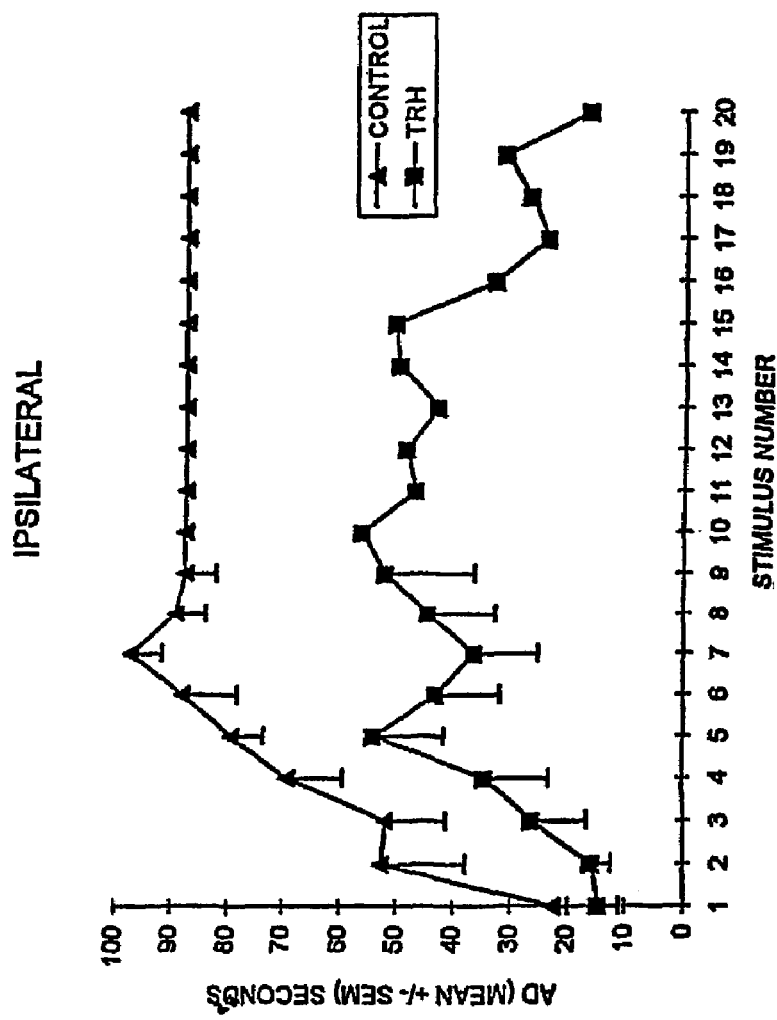
FIG. 3A is a graph illustrating afterdischarge duration (AD) in an ipsilateral amygdala as a function of stimulus number, which compares a control microstructure with a microstructure containing TRH.
Figure 3B:
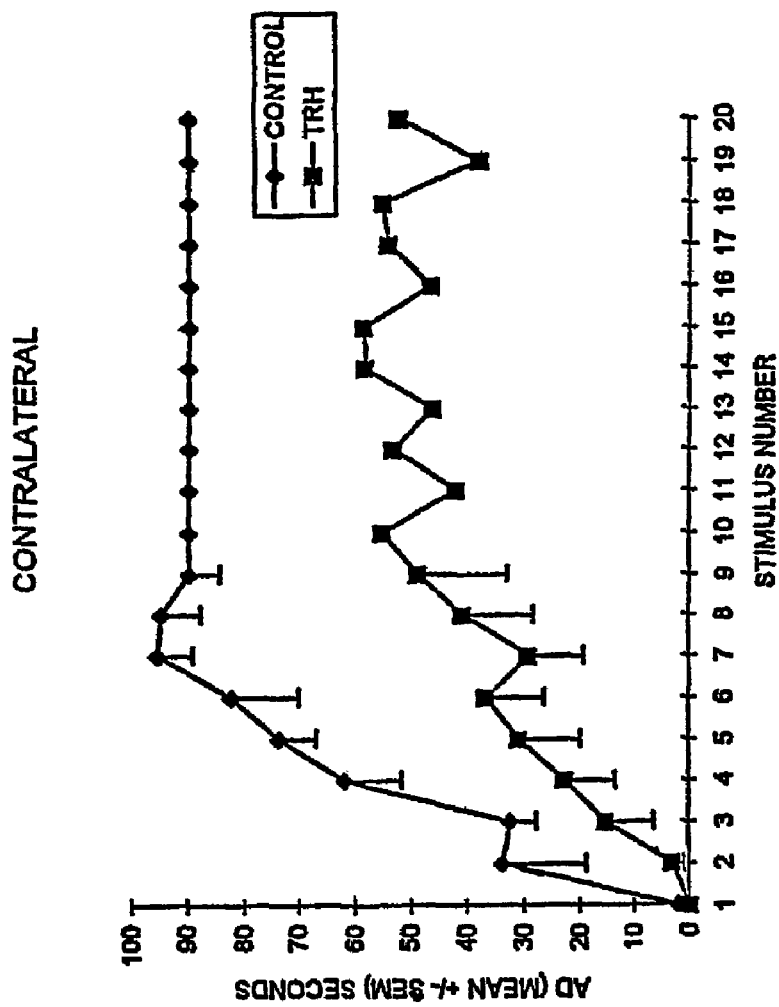
FIG. 3B is a graph illustrating afterdischarge duration (AD) in the contralateral amygdala as a function of stimulus number, which compares a control microstructure with a microstructure containing TRH.
Figure 4:
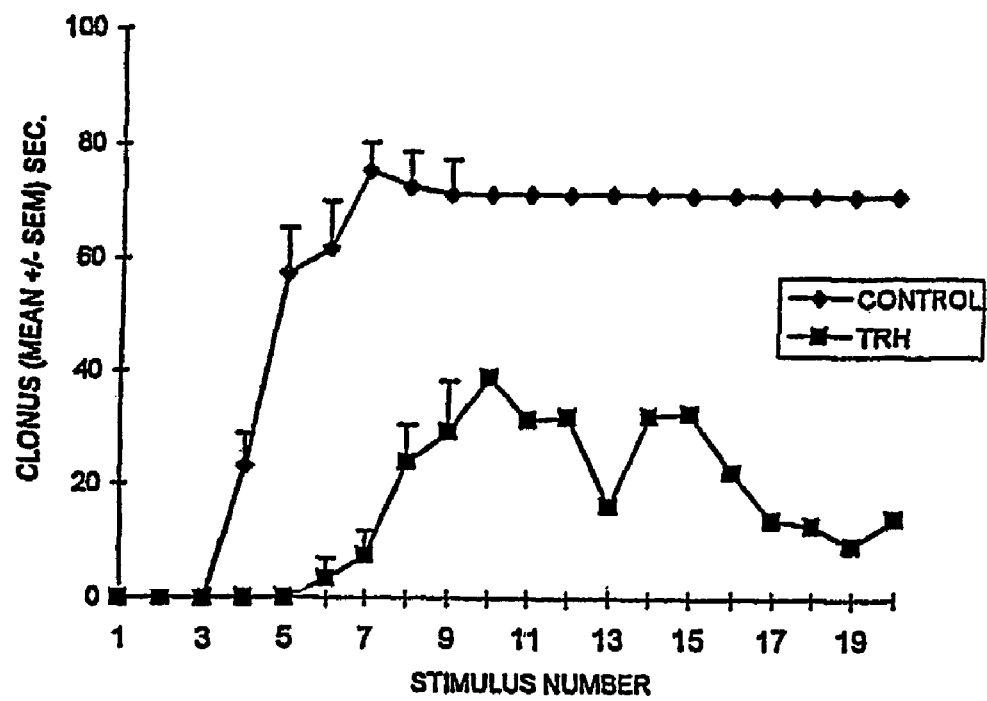
FIG. 4 is a graph of clonus as a function of stimulus number, which compares a control microstructure with a microstructure containing TRH.
Figure 5:
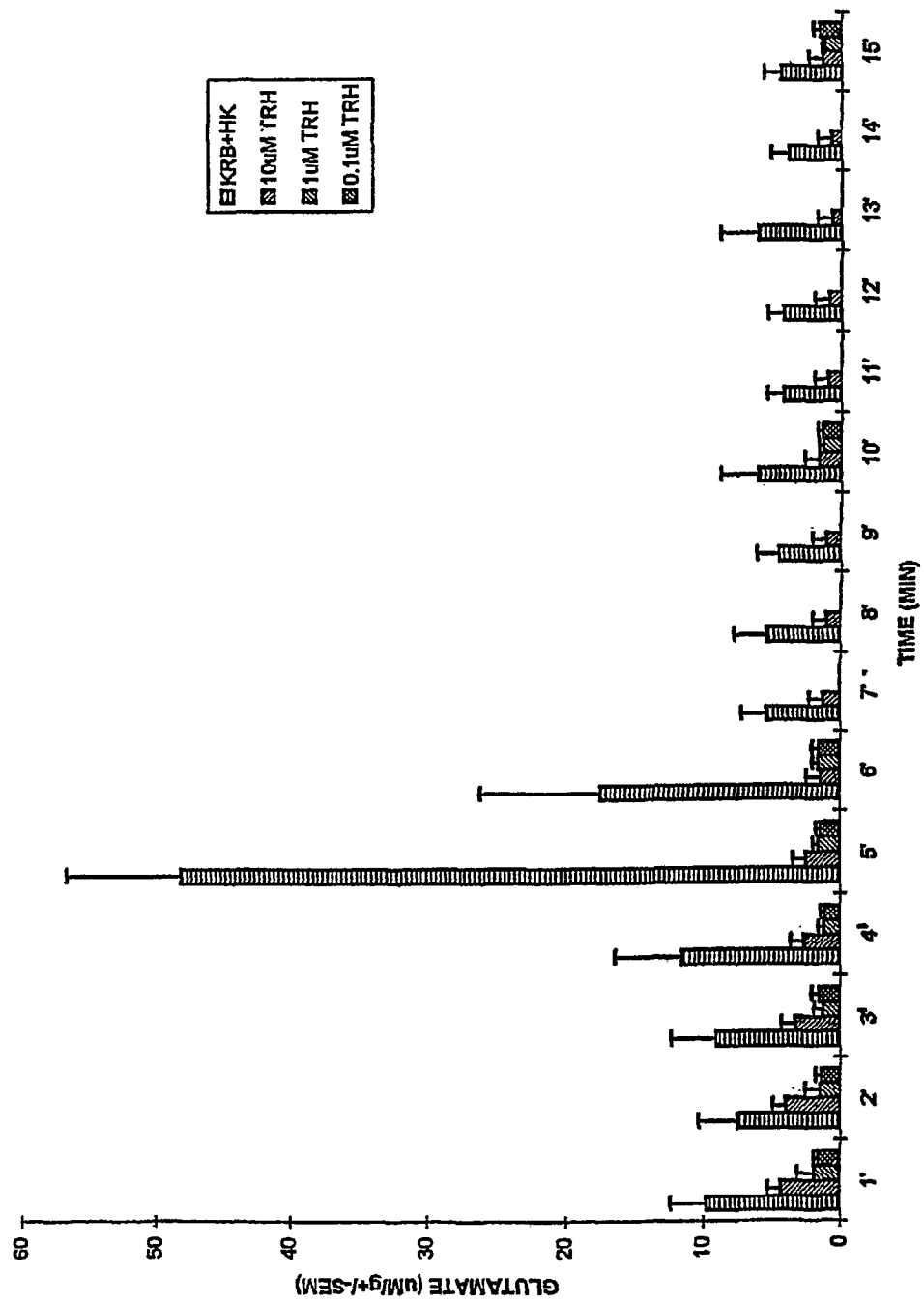
FIG. 5 is a graph of glutamate release as a function of time following high potassium stimulation (KRB+HK), which shows the inhibiting effect of TRH at different concentrations on glutamate release from rat hippocampal slices.

The data shown in FIGS. 2A and 2B demonstrate that a single TRH-microdisk significantly shortened the AD duration in both the stimulated (ipsilateral) ($P<0.02$) and unstimulated (contralateral) ($P<0.02$) amygdala as well. As seen in FIGS. 2A and 2B, in Panels A and B, the two tracings (A1 and B1) represent control rats (#82, #84) respectively, while, the lower two tracings (A2 & B2) represent TRH-microdisk rat #85. A 200 μA stimulation was given to the right amygdala (RA) of each animal, whereas, the (contralateral) left amygdala (LA) was unstimulated. S4 (Panel A) resulted in a prolonged AD duration (98 sec.) from both the RA and LA of the control animal (tracing A1). In marked contrast, tracing A2 depicts a short series of afterdischarges (AD's) (24 sec.) from the stimulated RA and an absence of stimulus transfer to the contralateral LA of the THR-microdisk animal. Behaviorally, S4 resulted in a Stage 3 response in the control rat (A1), whereas, only a Stage 1 response was observed in the THR microdisk animal (A2). S7 (Panel B), resulted in prolonged AD durations (>130 sec.) from both the RA and LA of the control animal (tracing B1). In marked contrast, tracing B2 depicts a much shorter series of AD's (28 sec.) from the stimulated RA and an absence of transfer to the contralateral LA of the TRH-microdisk animal. Behaviorally, S7 resulted in a Stage 5 generalized seizure in the control rat (B1), whereas, only a Stage 2 response was observed in the TRH microdisk animal (B2). WDS indicates Wet Dog Shakes.

The data clearly demonstrate that a biodegradable polymeric-TRH implant is capable of suppressing the development of kindling expressed as the number of stimulations required to reach each behavioral stage, and the number needed to reach full kindling. The TRH implant delayed kindling transfer to the contralateral amygdala as seen in FIGS. 2A and 2B, and significantly shortened the AD duration in both the ipsilateral (stimulated) and contralateral amygdala during kindling. The sustained release preparation substantially enhanced the antiepileptogenic and anticonvulsant efficacy of TRH over previously observed pharmacological studies. These results are striking and provide strong evidence for an antiepileptogenic/anticonvulsant function of TRH in the temporal lobe.

As noted above, the amygdala is a key site of kindled epileptogenesis and has widespread interconnections with cortical and subcortical areas. Therefore, it seems reasonable to conclude that sustained delivery of TRH in central nervous system loci is effective in substantially decreasing the level of excitability of amygdala efferents and it retards the rate of seizure spread (or generalization) throughout the brain for a prolonged period. Implanted microdisks (with or without TRH) had no effect on the ADT prior to kindling, and no apparent change in normal animal behavior was evident throughout the study. Therefore, it appears that the micro-constructs comprising an agonist and pharmaceutically acceptable carrier, as set forth herein, are safe for in vivo use.

Example 4

The present example illustrates preferred methods for long-term, intranasal TRH delivery using micro-constructs.

The rat kindling model of epilepsy described in Example 3 is useful in demonstrating the ability of the present inventive method to modulate release of at least one endogenous compound in vivo. As described in Example 3, bipolar electrodes are implanted bilaterally into the amygdalae as previously described. Five days after surgery, the afterdischarge threshold (ADT) is determined to verify that the subjects are suitable for kindling. Preferably, two experimental protocols are carried out using this kindling paradigm and intranasal polymeric-TRH delivery. One protocol is designed to demonstrate efficacy against kindling development (antiepileptogenic) by delivery of TRH micro-constructs during kindling. A second protocol is designed to demonstrate efficacy against seizures (antiepileptic) via intranasal delivery in fully kindled subjects.

Polymeric-TRH (FAD:SA) micro-constructs of the size and percent incorporation described herein are prepared and stored under refrigeration. Control micro-constructs are prepared as described herein with the exception that no TRH is incorporated into the micro-construct.

The anatomy of the rat nasal cavity is similar to other mammals. However, the rat nasal septum contains the so-called "septal window," so that the two-halves cannot be treated individually. The rat olfactory epithelium covers 50% of the total mucosal epithelium and is accessible by various techniques (see, for example, Gizurarson, *Acta Pharm. Nord.* 2:105-122 (1990)). TRH micro-constructs are suspended in saline and administered using a tubing-tipped microliter syringe. The applicator is inserted approximately 3 mm to 5 mm into each nostril. The suspension is delivered in a volume of from about 10 µl to about 13 µl to each nostril, which is equivalent to the volume to surface area ratio in man (Gizurarson, supra). The number of applications can vary depending on numerous factors such as, for example, TRH concentration and release rates.

For antiepileptic/anticonvulsant studies using the rat kindling model, subjects are fully kindled (3-5 consecutive stage 5 seizures) and housed for two weeks. Following the time-off period, control and test animals are intranasally administered control or TRH-incorporated micro-constructs. Application of the micro-constructs precedes the kindling (ictal) stimulus by approximately 45 to 55 minutes to allow for mucociliary absorption and anterograde axonal transport of the micro-constructs. Priming may also be used by giving three intranasal applications at 40 to 45 minute intervals prior to the first ictal stimulus. Subsequent applications of the micro-constructs are given approximately 45 to 55 minutes prior to each ictal stimulus. Behavioral (kindling stages 1 through 5) and EEG data are collected after each kindling (ictal) stimulus and compared to control subjects. The application times are based on most favorable conditions and may require adjustment depending on the animal model and particular embodiment of the present inventive method. The above-described protocols are designed, in part, to maximize the dose, delivery rate, and delivery interval for complete seizure suppression.

The optimal dose, delivery rate, and delivery interval determined from the antiepileptic studies described above are suitable for use in antiepileptogenic studies. Intranasal application of micro-constructs precedes the kindling stimulus by the optimal time, dose and interval. Priming may also be used to initially "load" the seizure focus. Subsequent applications of micro-constructs are given prior to each kindling stimulus until the subjects become fully kindled. Behavioral (kindling stages 1 through 5) and EEG data are collected after each kindling stimulus and compared to controls.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of modulating the release of at least one endogenous compound in vivo, wherein the method comprises delivering intranasally at least one micro-construct comprising at least one agonist and a pharmaceutically acceptable carrier to a locus comprising an agonist receptor and a heterologous receptor that are coupled to at least one common G-protein signaling molecule, wherein the micro-construct comprises a surface-eroding, non-bursting polymer of substantially uniform density and provides sustained release of the agonist provided by erosion of an exterior surface defined by the micro-construct to effectively up- or down-regulate at least one G-protein signaling molecule common to both the agonist receptor and the heterologous receptor to potentiate or desensitize the heterologous receptor in order to modulate release of at least one endogenous compound under the control of the heterologous receptor.

2. The method of claim 1, wherein the micro-construct is non-porous.

3. The method of claim 1, wherein the micro-construct is spherical.

4. A method of modulating the release of at least one endogenous compound in vivo, wherein the method comprises delivering intranasally at least one micro-construct comprising at least one agonist and a pharmaceutically acceptable carrier to a locus comprising an agonist receptor and a heterologous receptor that are coupled to at least one common G-protein signaling molecule,
wherein the micro-construct comprises a surface-eroding, non-bursting polymer of substantially uniform density and provides sustained release of the agonist provided by erosion of an exterior surface defined by the micro-construct to effectively up- or down-regulate at least one G-protein signaling molecule common to both the agonist receptor and the heterologous receptor to potentiate or desensitize the heterologous receptor in order to modulate release of at least one endogenous compound under the control of the heterologous receptor and wherein the micro-construct is non-spherical.

5. The method of claim 4, wherein the micro-construct is a microdisk.

6. The method of claim 4, wherein the non-spherical micro-construct defines a surface area decreasing with erosion at a rate less than $3.5\pi l(dl/dt)$ where l is a characteristic size of the micro-construct and (dl/dt) is the time rate of change of l.

7. The method of claim 1, wherein the heterologous receptor is desensitized and the release of the predetermined endogenous compound is inhibited.

8. The method of claim 1, wherein the heterologous receptor is potentiated and the release of the predetermined endogenous compound is increased.

9. The method of claim 1, wherein the polymer comprises a polyanhydride.

10. The method of claim 9, wherein the polymer is selected from the group consisting of polymeric oleic acid dimers, polymeric sebacic acid monomers, and combinations thereof.

11. The method of claim 1, wherein the endogenous compound is selected from the group consisting of a neurotransmitter, a neuropeptide, and a hormone.

12. The method of claim 11, wherein the neurotransmitter is selected from the group consisting of histamine, GABA, acetylcholine, serotonin, norepinephrine, epinephrine, glutamate, and dopamine.

13. The method of claim 11, wherein the neuropeptide is selected from the group consisting of thyrotropin-releasing hormone (TRH), somatostatin, neuropeptide Y (NPY), cholecystokinin (CCK), tachykinins, opiods, and neurotensin (NT).

14. The method of claim 11, wherein the hormone is selected from the group consisting of glucagon, ACTH, and melatonin.

15. The method of claim 7, wherein the endogenous compound is glutamate, the agonist is TRH, and the heterologous receptor comprises a glutamate receptor.

16. The method of claim 1, wherein the agonist comprises about 1% to about 60% of the micro-construct by weight.

17. The method of claim 16, wherein the agonist comprises about 1% to about 10% of the micro-construct by weight.

18. The method of claim 1, wherein concentration of agonist delivered to the locus is about $10^{-6}$ to about $10^{-12}$ M.

19. The method of claim 1, wherein at least one micro-construct is co-administered with a natural odorant.

20. The method of claim 1, wherein at least one micro-construct comprises at least one agonist and at least one neuronal transport facilitator.

21. The method of claim 15, wherein the locus is a central nervous system locus.

22. The method of claim 21, wherein a rate of seizure spread is controlled.

23. A method of modulating the release of at least one endogenous compound in vivo, wherein the method comprises delivering intranasally at least one micro-construct comprising a surface-eroding, non-bursting polymer of substantially uniform density and comprising at least one agonist and a pharmaceutically acceptable carrier to a locus comprising an agonist receptor and a heterologous receptor that are coupled to at least one common signaling molecule,
wherein the pharmaceutically acceptable carrier comprises a polymer selected from the group consisting of polyanhydride, polymeric oleic acid dimers, polymeric sebacic acid monomers, and combinations thereof, and
wherein the micro-construct provides sustained release of the agonist provided by erosion of an exterior surface defined by the micro-construct to effectively up- or down-regulate at least one G-protein signaling molecule common to both the agonist receptor and the heterologous receptor to potentiate or desensitize the heterologous receptor in order to modulate release of at least one endogenous compound under the control of the heterologous receptor.

24. A method of modulating the release of at least one endogenous compound in vivo selected from the group consisting of glucagon, ACTH, and melatonin, wherein the method comprises delivering intranasally at least one micro-construct comprising a surface-eroding, non-bursting polymer of substantially uniform density and comprising at least one agonist and a pharmaceutically acceptable carrier to a locus comprising an agonist receptor and a heterologous receptor that are coupled to at least one common signaling molecule,
wherein the micro-construct provides sustained release of the agonist provided by erosion of an exterior surface defined by the micro-construct to effectively up- or down-regulate at least one G-protein signaling molecule common to hot the agonist receptor and the heterologous receptor to potentiate or desensitize the heterologous receptor in order to modulate release of at least one endogenous compound under the control of the heterologous receptor.

* * * * *

UNITED STATES PATENT AND TRADEMARK OFFICE
CERTIFICATE OF CORRECTION

PATENT NO. : 7,229,635 B2
APPLICATION NO. : 10/258222
DATED : June 12, 2007
INVENTOR(S) : Michael J. Kubek It is certified that error appears in the above-identified patent and that said Letters Patent is hereby corrected as shown below:

Column 17, Line 17: --a comma-- should be inserted after the word "receptor".
Column 18, Line 51: "hot" should read --both--.

Signed and Sealed this

Twenty-eighth Day of August, 2007

JON W. DUDAS
*Director of the United States Patent and Trademark Office*